US00PP37204P2

(12) United States Plant Patent
van Diepen

(10) Patent No.: US PP37,204 P2
(45) Date of Patent: Jan. 13, 2026

(54) ***HELLEBORUS* PLANT NAMED 'Flevo 20-11-034'**

(50) Latin Name: ***Helleborus* x *ericsmithii* X *Helleborus* x *hybridus***
Varietal Denomination: Flevo 20-11-034

(71) Applicant: FlevoFlora B.V., Marknesse (NL)

(72) Inventor: Theodorus L. M. van Diepen, Marknesse (NL)

(73) Assignee: FLEVOFLORA B.V., Marknesse (NL)

( * ) Notice: Subject to any disclaimer, the term of this patent is extended or adjusted under 35 U.S.C. 154(b) by 0 days.

(21) Appl. No.: 19/224,780

(22) Filed: May 31, 2025

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

(56) References Cited

U.S. PATENT DOCUMENTS

PP24,720 P3 * 7/2014 Davey ..... A01H 6/72
Plt./439

* cited by examiner

*Primary Examiner* — Susan Mccormick Ewoldt
(74) *Attorney, Agent, or Firm* — C. Anne Whealy

(57) ABSTRACT

A new and distinct cultivar of *Helleborus* plant named 'Flevo 20-11-034', characterized by its upright and mounding plant habit; relatively vigorous growth habit; dark green-colored leaves; freely flowering habit; purplish red-colored flower sepals; and good garden performance.

2 Drawing Sheets

Figure 1:
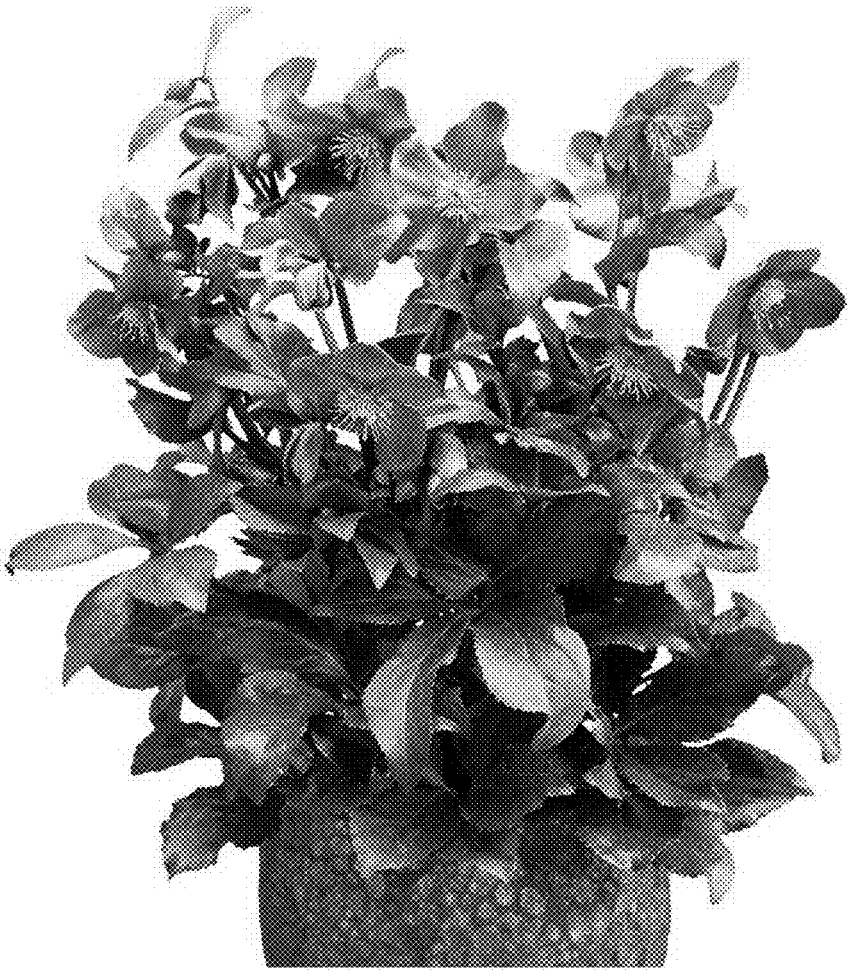

Botanical designation: *Helleborus* x *ericsmithii* X *Helleborus* x *hybridus*.

Cultivar denomination: 'FLEVO 20-11-034'.

CROSS-REFERENCED TO CLOSELY-RELATED APPLICATIONS

A European Community Plant Breeder's Rights application for the instant plant was filed by the Applicant/Assignee of the instant application, FlevoFlora B.V. of Marknesse, The Netherlands on Sep. 30, 2024, application number 2024/2292. Foreign priority is not claimed to this European Community Plant Breeder's Rights application.

BACKGROUND OF THE INVENTION

The present invention relates to a new and distinct cultivar of *Helleborus* plant, botanically known as *Helleborus* x *ericsmithii* X *Helleborus* x *hybridus*, commonly referred to as an interspecific hybrid Hellebore and hereinafter referred to by the name 'Flevo 20-11-034'.

The new *Helleborus* plant is a product of a planned breeding program conducted by the Inventor in Marknesse, The Netherlands. The objective of the breeding program was to create new uniformly mounding and freely-flowering *Helleborus* plants with attractive leaves and flowers.

The new *Helleborus* plant originated from a cross-pollination conducted by the Inventor in Marknesse, The Netherlands in December 2020 of a proprietary selection of *Helleborus* x *ericsmithii* identified as code number 1728VD, not patented, as the female, or seed, parent with an unidentified proprietary selection of *Helleborus* x *hybridus*, not patented, as the male, or pollen, parent. The new *Helleborus* plant was discovered and selected by the Inventor as a single flowering plant from within the progeny of the stated cross-pollination grown in a controlled greenhouse environment in Marknesse, The Netherlands in January 2023.

Asexual reproduction of the new *Helleborus* plant by in vitro meristem culture in a controlled greenhouse environment in Marknesse, The Netherlands since May 2023, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Flevo 20-11-034'. These characteristics in combination distinguish 'Flevo 20-11-034' as a new and distinct *Helleborus* plant:

1. Upright and mounding plant habit.
2. Relatively vigorous growth habit.
3. Dark green-colored leaves.
4. Freely flowering habit.
5. Purplish red-colored flower sepals.
6. Good garden performance.

Plants of the new *Helleborus* differ primarily from plants of the female parent selection in the following characteristics:

1. Plants of the new *Helleborus* are taller than plants of the female parent selection.
2. Plants of the new *Helleborus* flower earlier than plants of the female parent selection.

3. Flower sepals of plants of the new *Helleborus* are purplish red in color whereas flower sepals of plants of female parent selection are greenish white in color.

Plants of the new *Helleborus* can be compared to plants of *Helleborus* x *hybridus* 'ABCRD02', disclosed in U.S. Plant Pat. No. 24,720. In side-by-side comparisons, plants of the new *Helleborus* differ from plants of 'ABCRD02' in the following characteristics:

1. Leaflets of plants of the new *Helleborus* have less distinct venation than leaflets of plants of 'ABCRD02'.
2. Plants of the new *Helleborus* flower earlier than plants of 'ABCRD02'.
3. Plants of the new *Helleborus* are more freely flowering than plants of 'ABCRD02'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'Flevo 20-11-034' grown in a container.

Figure 2:
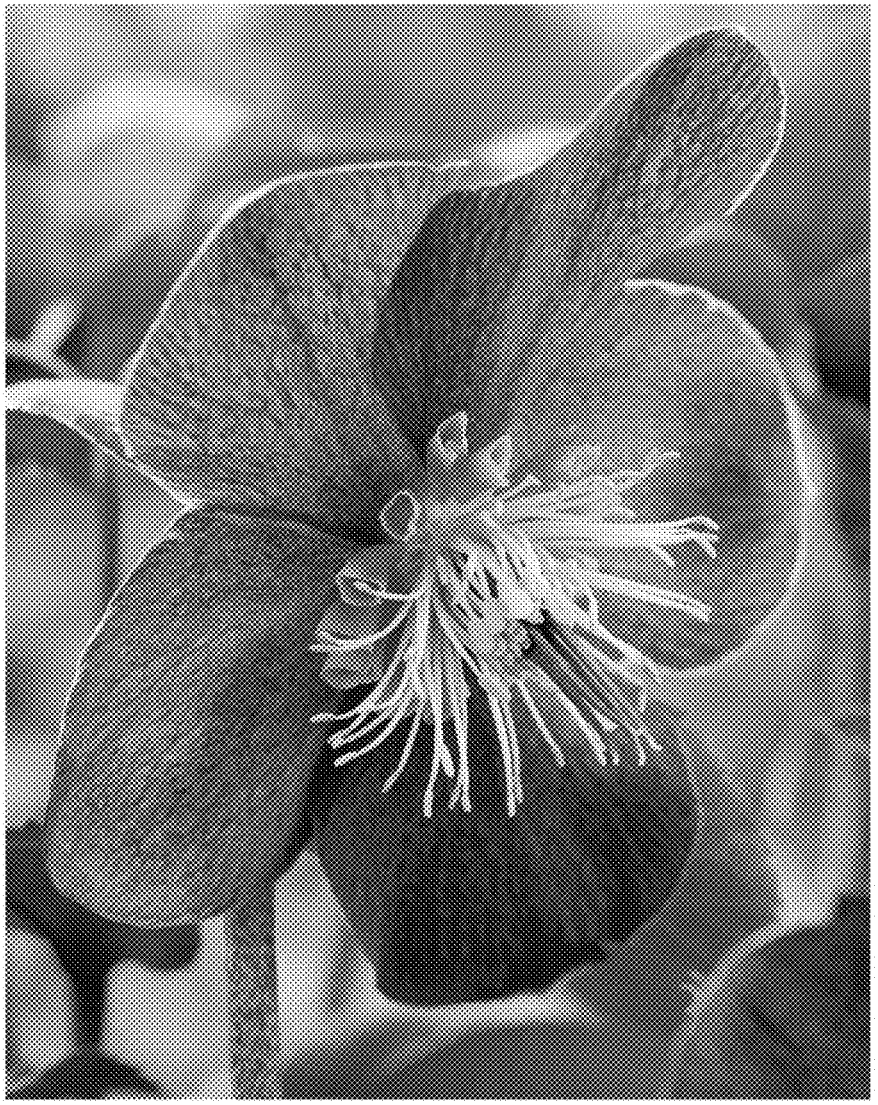

The photograph on the second sheet (FIG. 2) is a close-up view of a typical flower of 'Flevo 20-11-034'.

DETAILED BOTANICAL DESCRIPTION

The aforementioned photographs and following observations, measurements and values describe plants grown in 19-cm containers during the winter in a glass-covered greenhouse in Marknesse, The Netherlands and under cultural practices typical of commercial *Helleborus* production. During the production of the plants, day temperatures ranged from 12° C. to 31° C. and night temperatures ranged from 3° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'Flevo 20-11-034'.

Parentage:

*Female, or seed, parent*.—Proprietary selection of *Helleborus* x *ericsmithii* identified as code number 1728VD, not patented.

*Male, or pollen, parent*.—Unidentified proprietary selection of *Helleborus* x *hybridus*, not patented.

Propagation:

*Type*.—By in vitro meristem culture.

*Time to initiate roots, winter*.—About 50 days at temperatures about 12° C.

*Time to produce a rooted young plant, winter*.—About 20 weeks at temperatures about 2° C. to 14° C.

*Root description*.—Fleshy, variable in thickness; typically white to greenish brown in color, actual color of the roots is dependent on substrate composition, water quality, fertilizer type and formulation, substrate temperature and physiological age of roots.

*Rooting habit*.—Not freely branching; sparse.

Plant description:

*Plant and growth habit*.—Herbaceous perennial; upright and mounding plant habit; overall plant shape, roughly flattened globular; relatively vigorous growth habit and moderate growth rate; leaves arranged in basal rosettes; flowers held within and above the foliar plane.

*Plant height, soil level to top of foliar plane*.—About 33.5 cm.

*Plant height, soil level to top of floral plane*.—About 34.8 cm.

*Plant diameter* (*area of spread*).—About 32.9 cm.

Leaf description:

*Arrangement*.—Leaves arranged alternately in a basal rosette; leaves palmately compound with typically five leaflets per leaf.

*Leaf length*.—About 21.6 cm.

*Leaf width*.—About 26.4 cm.

*Leaflet length*.—About 16.7 cm.

*Leaflet width*.—About 6.2 cm.

*Leaf shape*.—Palmately compound; roughly reniform in outline.

*Leaflet shape*.—Ovate.

*Leaflet apex*.—Acute.

*Leaflet base*.—Attenuate.

*Leaflet margin*.—Dentate to serrate; slightly undulate.

*Leaflet texture and luster, upper and lower surfaces*.—Smooth, glabrous; leathery; glossy.

*Leaflet venation pattern*.—Pinnate.

*Leaflet color*.—Developing leaflets, upper surface: Close to NN147A; venation, close to 187B. Developing leaflets, lower surface: Close to 137A; midvein, close to 187C. Fully expanded leaflets, upper surface: Close to 137A; venation, close to 144A. Fully expanded leaflets, lower surface: Close to 137C; venation, close to 187B.

*Petioles*.—Length: About 15.6 cm. Diameter: About 5 mm to 7 mm. Texture, upper and lower surfaces: Smooth, glabrous. Color, upper surface: Close to 143B densely covered with fine dots, close to 185B. Color, lower surface: Close to 143B and towards the base, close to 184C; densely covered with fine dots, close to 185B.

Flower description:

*Flower shape and habit*.—Single rotate cyanthiform flowers arranged in loosely-branched terminal and axillary cymes; freely flowering habit with typically about two to five flowers developing per cyme and about 112 flowers developing during the first flowering season; flowers face outwardly to nodding.

*Fragrance*.—None detected.

*Natural flowering season*.—Plants begin flowering about nine months after planting young plants; flower continuously from November to April in The Netherlands.

*Flower longevity on the plant*.—About ten days; sepals are persistent and other flower parts are not persistent.

*Flower buds*.—Length: About 2.9 cm. Diameter: About 1.4 cm. Shape: Broadly ovoid. Texture and luster: Smooth, glabrous; matte. Color: Close to 187B.

*Inflorescence height*.—About 29.1 cm.

*Inflorescence diameter*.—About 22.3 cm.

*Flower diameter*.—About 10.8 cm.

*Flower depth* (*height*).—About 2.4 cm.

*Petals*.—None observed; transformed into nectaries.

*Sepals*.—Quantity and arrangement: About five arranged in a single whorl. Length: About 4.2 cm to 5.9 cm. Width: About 5.1 cm. Shape: Broadly ovate. Apex: Elliptic to obtuse. Base: Cuneate. Margin: Entire; slightly undulate. Texture and luster, upper surface: Smooth, glabrous; matte. Texture and luster, lower surface: Smooth, glabrous; slightly glossy. Color: When opening, upper surface: Close to 71A. When opening, lower surface: Close to 71A; towards the margins, tinged with close to 185B. Fully opened, upper surface: Close to 185B; towards the margins, tinged with close to 187A; color becoming closer to 187B with subsequent development. Fully opened, lower surface: Close to 187C; color becoming closer to 184A and tinged towards the margins with close to 177A with subsequent development.

*Peduncles*.—Length: About 23.8 cm. Diameter: About 6 mm to 10 mm. Texture and luster: Smooth, glabrous; moderately glossy. Color: Close to 147B flushed with close to 186C with fine dots, close to 187B.

*Pedicels*.—Length: About 4.3 cm to 8.6 cm. Diameter: About 4 mm. Texture and luster: Smooth, glabrous; moderately glossy. Color: Close to 144A.

*Reproductive organs*.—Stamens: Quantity per flower: About 100.Filament length: About 1.8 cm. Filament color: Close to 187A; distally, close to NN155D. Anther shape: Reniform; basifixed. Anther size: About 2 mm by 3 mm. Anther color: Close to 4B. Pollen amount: Scarce. Pollen color: Close to 2D. Pistils: Quantity per flower: About four to five. Pistil length: About 1.1 cm. Stigma diameter: About 0.2 mm. Stigma shape: Club-shaped. Stigma color: Close to 149D. Style length: About 1.3 cm. Style color: Close to 187D. Ovary color: Close to 187B.

*Nectaries*.—Quantity per flower: About ten. Length: About 9 mm. Width: About 3.5 mm. Shape: Tubular, flattened. Texture and luster, inner and outer surfaces: Smooth, glaucous; matte. Color: When opening, inner and outer surfaces: Close to NN137C; color does not change with subsequent development. Fully opened, inner and outer surfaces: Close to 136C and distally, close to 151A; color becoming entirely close to 136C with subsequent development. Seeds and fruits: To date, seed and fruit development have not been observed on plants of the new *Helleborus*.

Garden performance & temperature tolerance: Plants of the new *Helleborus* have been observed to have good garden performance and to tolerate rain and wind. Plants of the new *Helleborus* are suitable for USDA Hardiness Zones 4 to 9 and have been observed to tolerate high temperatures about 34° C.

Pathogen & pest resistance: To date, plants of the new *Helleborus* have not been observed to be resistant to pathogens and pests common to *Helleborus* plants.

It is claimed:

1. A new and distinct *Helleborus* plant named 'Flevo 20-11-034' as herein illustrated and described.

* * * * *